United States Patent
Duke

(10) Patent No.: US 8,532,764 B2
(45) Date of Patent: Sep. 10, 2013

(54) POST-DOWNLOAD PATIENT DATA PROTECTION IN A MEDICAL DEVICE

(75) Inventor: Steven B. Duke, Bothell, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 12/574,380

(22) Filed: Oct. 6, 2009

(65) Prior Publication Data

US 2010/0023076 A1 Jan. 28, 2010

Related U.S. Application Data

(62) Division of application No. 11/348,098, filed on Feb. 6, 2006, now abandoned.

(51) Int. Cl.
*A61N 1/00* (2006.01)
*G06Q 50/00* (2012.01)

(52) U.S. Cl.
USPC ............... 607/5; 607/30; 607/31; 705/3

(58) Field of Classification Search
USPC .................. 607/5, 30–31; 705/3
See application file for complete search history.

(56) References Cited

U.S. PATENT DOCUMENTS

| | | | |
|---|---|---|---|
| 4,635,639 A | 1/1987 | Hakala et al. |
| 4,916,439 A | 4/1990 | Estes et al. |
| 5,012,411 A | 4/1991 | Policastro et al. |
| 5,419,336 A | 5/1995 | Margison |
| 5,549,115 A | 8/1996 | Morgan et al. |
| 5,549,659 A | 8/1996 | Johansen et al. |
| 5,593,426 A | 1/1997 | Morgan et al. |
| 5,674,252 A | 10/1997 | Morgan et al. |
| 5,680,864 A | 10/1997 | Morgan et al. |
| 5,683,423 A | 11/1997 | Post |
| 5,715,823 A | 2/1998 | Wood et al. |
| 5,749,902 A | 5/1998 | Olson et al. |
| 5,749,913 A | 5/1998 | Cole |

(Continued)

FOREIGN PATENT DOCUMENTS

| | | |
|---|---|---|
| EP | 0 801 959 A3 | 12/1998 |
| WO | WO 00/70889 | 11/2000 |
| WO | WO 02/060529 A2 | 8/2002 |

OTHER PUBLICATIONS

PCT Written Opinion and International Search Report, International Application No. PCT/US07/61628, mailed Nov. 29, 2007.

*Primary Examiner* — Nicole F Lavert
(74) *Attorney, Agent, or Firm* — Marger Johnson & McCollom, P.C.

(57) ABSTRACT

The disclosure describes techniques for protecting patient data stored in a medical device, such as an external defibrillator. The patient data may be transferred, or downloaded, from the medical device to another device, such as to a computing device for storage or analysis. In response to the download, the medical device may protect the patient data so that at least subset of users can no longer access the patient data. Patient data may be protected by modifying the data form, encrypting the data, moving the data to another memory module, password protecting the patient data, or modifying an access control list associated with the patient data. While the patient data may also be deleted as a technique for protecting the data, not deleting the data may allow the data to be recovered at a later time by an authorized user, i.e., a user not part of the subset.

24 Claims, 5 Drawing Sheets

(56) References Cited

U.S. PATENT DOCUMENTS

| | | | |
|---|---|---|---|
| 5,782,878 | A | 7/1998 | Morgan et al. |
| 5,787,155 | A | 7/1998 | Luna |
| 5,836,993 | A | 11/1998 | Cole |
| 5,857,967 | A | 1/1999 | Frid et al. |
| 5,891,046 | A | 4/1999 | Cyrus et al. |
| 5,891,049 | A | 4/1999 | Cyrus et al. |
| 5,899,866 | A | 5/1999 | Cyrus et al. |
| 5,921,938 | A | 7/1999 | Aoyama et al. |
| 5,950,632 | A | 9/1999 | Reber et al. |
| 5,951,485 | A | 9/1999 | Cyrus et al. |
| 5,999,493 | A | 12/1999 | Olson |
| 6,024,699 | A | 2/2000 | Surwit et al. |
| 6,041,257 | A | 3/2000 | MacDuff et al. |
| 6,047,207 | A | 4/2000 | MacDuff et al. |
| 6,057,758 | A | 5/2000 | Dempsey et al. |
| 6,111,505 | A | 8/2000 | Wagener |
| 6,141,584 | A | 10/2000 | Rockwell et al. |
| 6,144,922 | A | 11/2000 | Douglas et al. |
| 6,150,951 | A | 11/2000 | Olejniczak |
| 6,157,313 | A | 12/2000 | Emmermann |
| 6,183,417 | B1 | 2/2001 | Geheb et al. |
| 6,201,992 | B1 | 3/2001 | Freeman |
| 6,301,501 | B1 | 10/2001 | Cronin et al. |
| 6,301,502 | B1 | 10/2001 | Owen et al. |
| 6,304,780 | B1 | 10/2001 | Owen et al. |
| 6,321,113 | B1 | 11/2001 | Parker et al. |
| 6,323,782 | B1 | 11/2001 | Stephens et al. |
| 6,334,070 | B1 | 12/2001 | Nova et al. |
| 6,336,900 | B1 | 1/2002 | Alleckson et al. |
| 6,360,120 | B1 | 3/2002 | Powers et al. |
| 6,374,138 | B1 | 4/2002 | Owen et al. |
| 6,381,492 | B1 | 4/2002 | Rockwell et al. |
| 6,405,083 | B1 | 6/2002 | Rockwell et al. |
| 6,427,083 | B1 | 7/2002 | Owen et al. |
| 6,438,417 | B1 | 8/2002 | Rockwell et al. |
| 6,493,581 | B2 | 12/2002 | Russell |
| 6,524,241 | B2 | 2/2003 | Iliff |
| 6,594,634 | B1 | 7/2003 | Hampton et al. |
| 6,597,948 | B1 | 7/2003 | Rockwell et al. |
| 6,668,192 | B1 | 12/2003 | Parker et al. |
| 6,747,556 | B2 | 6/2004 | Medema et al. |
| 2002/0103508 | A1 | 8/2002 | Mathur |
| 2002/0123673 | A1 | 9/2002 | Webb et al. |
| 2003/0025602 | A1 | 2/2003 | Medema et al. |
| 2003/0058097 | A1 | 3/2003 | Saltzstein et al. |
| 2003/0065536 | A1 | 4/2003 | Hansen et al. |
| 2003/0095648 | A1* | 5/2003 | Kaib et al. ............... 379/106.02 |
| 2003/0109904 | A1 | 6/2003 | Silver et al. |
| 2003/0212311 | A1 | 11/2003 | Nova et al. |
| 2004/0049233 | A1 | 3/2004 | Edwards |
| 2004/0212344 | A1 | 10/2004 | Tamura et al. |
| 2005/0192844 | A1 | 9/2005 | Esler |
| 2005/0283210 | A1* | 12/2005 | Blischak et al. ................ 607/60 |
| 2006/0074983 | A1* | 4/2006 | Jones ........................ 707/104.1 |
| 2006/0206361 | A1* | 9/2006 | Logan, Jr. ........................ 705/3 |

\* cited by examiner

POST-DOWNLOAD PATIENT DATA PROTECTION IN A MEDICAL DEVICE

CROSS REFERENCE TO RELATED APPLICATIONS

This application is a divisional of U.S. application Ser. No. 11/348,098, filed Feb. 6, 2006, now abandoned, and previously published as U.S. Application Publication No. 2010-0023076 A1, the entire content of which is incorporated herein by reference.

TECHNICAL FIELD

The invention relates to medical devices and, more particularly, to medical device data management.

BACKGROUND

An external defibrillator delivers energy to a heart of a patient via electrodes placed upon the patient's chest. Often, external defibrillators are used to deliver energy in the form of a defibrillation pulse to a heart that is undergoing ventricular fibrillation and has lost its ability to contract. Ventricular fibrillation is particularly life threatening because activity within the ventricles of the heart is so uncoordinated that virtually no pumping of blood takes place. If untreated, the patient whose heart is undergoing fibrillation may die within a matter of minutes.

An electrical pulse delivered to a fibrillating heart may depolarize the heart and cause it to reestablish a normal sinus rhythm. In some cases, the patient may need multiple pulses, and the external defibrillator may deliver different quantities of energy with each defibrillation pulse. Further, the defibrillator may provide additional or alternative therapies to the patient, such as cardioversion or pacing therapy. As examples, the external defibrillator may be an automated external defibrillator (AED) used by a first responder or bystander to treat the patient, or a more fully-featured defibrillator/monitor used by paramedics.

In some cases, the defibrillator collects and saves information related to the patient. This patient data may include personal and physiological data. Personal data may include the patient's name, age, sex, medical conditions, prescribed medications, or circumstances surrounding the need for treatment with the defibrillator. Physiological data may include the patient's heart rate, blood pressure, electrocardiogram (ECG), or other measured data related to the patient's condition. The patient data may also include a record of therapies provided to the patient, as well as audio recorded during the treatment of the patient. The patient data stored in the defibrillator may be downloaded to another device, such as a computing device for review, generation of a "run report" related to the treatment of the patient, or integration into the patient's long-term medical records.

SUMMARY

The disclosure is directed to techniques for protecting patient data stored in a medical device, such as an external defibrillator. Patient data stored by such devices may be sensitive and personal in nature. Further, the Health Insurance Portability and Accountability Act of 1996 (HIPPA) set for "Standards for Individually Identifiable Health Information," which may apply to at least some patient data stored by such devices. Accordingly, any potential public or unauthorized disclosure of the patient data stored by such medical devices should be avoided.

Some existing external defibrillators and other medical devices store patient data for a potentially indefinite period of time, e.g., until it is overwritten by new patient data. The patient data may be accessible to any user who has physical access to the device. The accessibility of the data may be a particular problem in the case of an automated external defibrillator (AED), which may be physically available to a large pool of trained first responders, or the general public in public locations such as airports, stadiums, shopping malls, or other places of business.

As discussed above, the patient data stored by an external defibrillator may be downloaded to a computing device. Generally, such downloads occur as a matter of course or protocol a short time after the external defibrillator is done being used to treat the patient, e.g., when the first responder returns to a dispatch center or station with an external defibrillator after its use. Further, after such a download, the patient information is generally not needed or used at the external defibrillator.

Accordingly, in response to a download of patient data, embodiments of invention protect the patient data stored within the external defibrillator. The patient data within the external defibrillator is protected such that it is inaccessible to at least a subset of the users that had previously been able to access the data. The protection of the patient data within the external defibrillator may take many forms. For example, patient data within the external defibrillator may be protected by modifying the form of the data, encrypting the data, moving the data to another memory module, password protecting the data, modifying an access control list associated with the patient data, or deleting the data. While the patient data may be deleted as a technique for protecting the data, not deleting the data may allow the data to be recovered at a later time by an authorized user, i.e., a user not part of the subset, if necessary.

The protection of the patient data may, but does not necessarily occur upon completion of the download. The protection of the patient data may, for example, occur upon receipt of an acknowledgment from the computing device that downloads the data. Further, the protection may be a user-configurable feature. For example, a user may provide an instruction or other input indicating whether the patient data should be protected in response to a download.

Embodiments of the invention may protect patient data stored within the external defibrillator that initially collected the data, as described. Embodiments of the invention may additionally or alternatively protect the patient data collected by an external defibrillator when stored within other medical devices that receive the patient data, such as various computing devices or networked servers. The other medical devices may protect the patient data in substantially the same manner described above with respect to the external defibrillator, and in response to further downloading the patient data to yet another device.

In one embodiment, the invention is directed to a method comprising storing patient data collected by an external defibrillator during treatment of a patient in a medical device, allowing users to access the patient data stored in the medical device, downloading the patient data from the medical device to another device and, in response to downloading the patient data, protecting the patient data in the medical device such that the protected patient data is inaccessible to at least a subset of the users.

In another embodiment, the invention is directed to a medical device comprising a memory, a communications circuit and a processor. The memory stores patient data collected by an external defibrillator during treatment of a patient. The communications circuit is configured to communicate with another device. The processor allows users to access the patient data stored in the memory, controls the communications circuit to download the patient data to the other device and, in response to the download, protects the patient data in the memory such that the protected patient data is inaccessible to at least a first subset of the users.

In another embodiment, the invention is directed to a computer readable medium comprising instructions that cause a processor to store patient data collected by an external defibrillator during treatment of a patient within a medical device, allow users to access the patient data stored in the medical device, download the patient data to another device; and in response to the download, protect the patient data in the first device such that the protected patient data is inaccessible to at least a first subset of the users.

In various embodiments, the disclosure may provide one or more advantages. For example, protecting patient data in a medical device may provide greater security to sensitive information of a patient when multiple users have access to the medical device. Also, protecting the patient data once it is downloaded may allow only a single download of the patient data without further authorization or the intervention of an authorized user.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
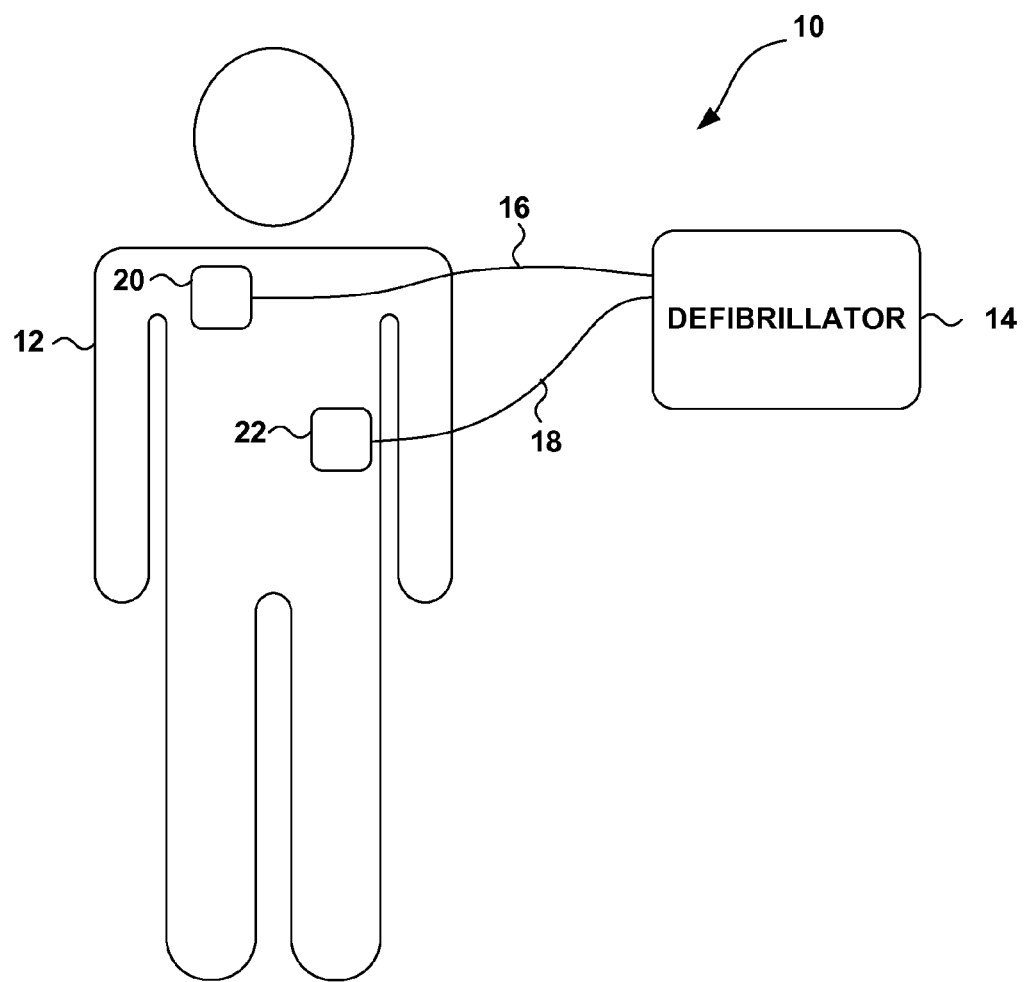
FIG. 1 is a conceptual diagram illustrating an example system that includes an external defibrillator device that collects and stores patient data.

FIG. 1 is a conceptual diagram illustrating an example system 10 that includes an example external defibrillator 14 that collects and stores patient data. External defibrillator 14 may, but does not necessarily, take the form of an automated external defibrillator (AED). Defibrillator 14 is connected to a patient 12 by leads 16 and 18, and electrode pads 20 and 22. Pads 20 and 22 are placed on the bare skin of patient 12, and may be affixed to the patient with an adhesive.

Pads 20 and 22 include electrodes through which defibrillator 14 may detect electrical signals within patient 12 and deliver electrical therapy to patient 12. In AED embodiments, external defibrillator 14 may monitor the electrocardiogram (ECG) of patient 12 based on the signals detected via pads 20 and 22, and determine the functionality of the heart. Depending on the condition of the heart, external defibrillator 14 in automated embodiments may deliver instructions to the rescuer such as whether or not to deliver an electrical defibrillation pulse to treat a detected ventricular fibrillation. In other AED embodiments, the defibrillator may automatically deliver a defibrillation pulse based on the ECG analysis. Further, in manual embodiments of defibrillator 14, the rescuer may determine whether a defibrillation pulse should be delivered based on a displayed ECG detected via pads 20 and 22.

Defibrillator 14 may also be capable of monitoring other physiological parameters of patient 12, and delivering other therapies to the patient. For example, defibrillator 14 may include or be coupled to sensors to monitor blood pressure, blood oxygen saturation, respiration, or expired carbon dioxide. Further, defibrillator 14 may be capable of delivering cardioversion or pacing therapies via pads 20 and 22, or controlling delivery of cardiopulmonary resuscitation (CPR) by the rescuer or an automated device.

The patient data collected by defibrillator 14 may include information describing the therapies delivered to patient 12, including the times that the therapies were delivered. The patient data may also include physiological parameter information, including information relating to the times that the physiological parameter information was recorded. In some embodiments, defibrillator 14 may include a microphone or the like through which it may detect audible sound occurring during treatment of patient 12. In such embodiments, defibrillator 14 may include an audio recording as part of the patient data. Defibrillator 14 may collect other personal information of patient 12 such as name, height, weight, age, prescribed medications, medical conditions, location, or any other information that may be desired. This personal information, part of the patient data, may be entered into the defibrillator by the rescuer through the use of a user interface (not shown in FIG. 1).

Figure 2:
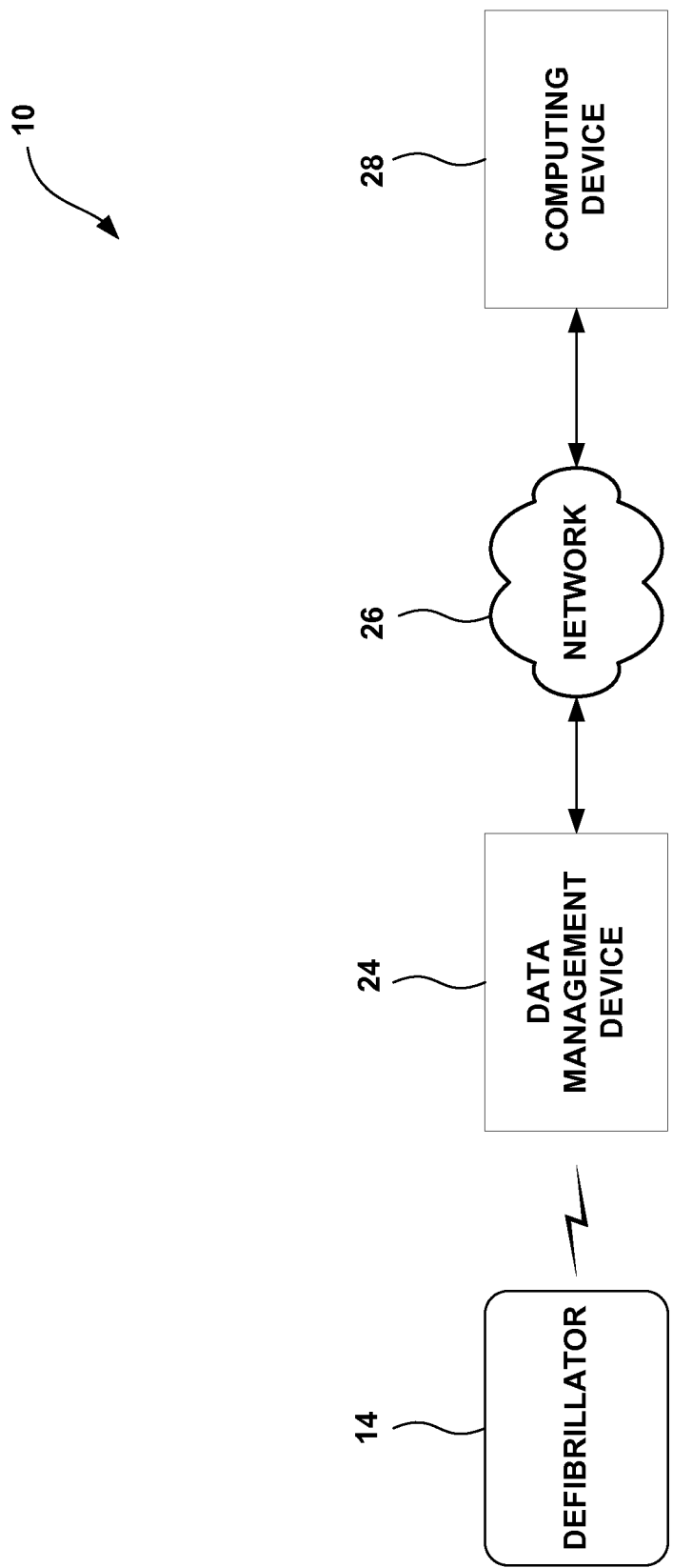
FIG. 2 is a block diagram further illustrating the example system of FIG. 1.

FIG. 2 is a block diagram further illustrating system 10. As discussed above, patient data stored in defibrillator 14 may be downloaded to another device, such as a computing device 28. As examples, the patient data may be downloaded from the defibrillator to the other device for review, generation of a "run report" related to the treatment of the patient, or integration into the long-term medical records of patient 12. Computing device 28 may be any of a variety of devices, such as a handheld, laptop, or desktop computer, or a network server.

In the illustrated embodiment, external defibrillator 14 downloads the patient data to computing device 28 via an intermediate data management device (DMD) 24 and a network 26. Therefore, DMD 24 is an intermediary between defibrillator 14 and computing device 28, and may protect the patient data when the data is transferred between devices in the same or a similar manner to defibrillator 14. DMD 24 may also be a computing device, such as handheld, laptop, or desktop computer, or a network server. Alternatively, DMD 24 may be a base or docking station for the external defibrillator. DMD 24 may have communication circuitry to facilitate local communication with defibrillator 14, as well as network communication with computing device 28.

In the illustrated embodiment, defibrillator 14 and DMD 24 communicate wirelessly, e.g., via an infrared or radio-frequency medium. Nonetheless, the invention is not limited to any particular form of communication between defibrillator 14, DMD 26, network 26 and computing device 28, or any particular form of communication within network 26. Network 26 may be a local area network (LAN) or a wide area network (WAN), such as the Internet.

In some embodiments, DMD 24 may simply forward the patient data to computing device 28. In other embodiments, DMD 24 may store the patient data, and may also provide functionality associated herein with computing device 28, such as generation of run reports, or other processing or management of the patient data. Further, in some embodiments, DMD 24 may allow additional patient data to be entered by a user and combined with the patient data collected by defibrillator 14. For example, DMD 24 may be a handheld or other type of computing device used by an emergency medical technician (EMT) or first responder to input patient data during or after treatment of patient 12, and to combine the inputted data with patient data downloaded from defibrillator 14 during or after treatment of patient 12.

Further, in some embodiments, computing device 28 may download the patient data to other devices. For example, computing device 28 may take the form of a network server that downloads the data to a particular computer or system, which may be associated with a hospital or a manufacturer of defibrillator 14, for archival, review by clinicians or engineers, or integration into the long-term medical records of patient 12. Moreover, other embodiments need not include network 26 or DMD 24. In such embodiments, defibrillator 14 may simply download patient data directly to computing device 28.

In any event, in response to a download of patient data from defibrillator 14 to another device, such as DMD 24 or computing device 28, defibrillator 14 protects the patient data stored in the defibrillator. More particularly, defibrillator 14 protects the patient data such that at least a subset of users who could previously access the patient data stored in the defibrillator are no longer able to access the patient data in the defibrillator. The protection of the patient data may, but does not necessarily occur upon completion of the download from defibrillator 14. Defibrillator 14 may, for example, protect the patient data upon receipt of an acknowledgment from DMD 24 or computing device 28 that the data has been successfully downloaded. When protected, the patient data may be inaccessible via a user interface of defibrillator 14 and/or via computing devices that communicate with the defibrillator.

Defibrillator 14 may protect the patient data stored therein in a variety of ways. For example, defibrillator 14 may protect the patient data therein by modifying the form of the data, encrypting the data, moving the data to another memory module, password protecting the data, modifying an access control list associated with the patient data, or deleting the data. When defibrillator 14 protects the patient data by deleting the patient data, the patient data is no longer available to any users via the defibrillator. However, when defibrillator 14 protects the patient data using other techniques, a subset of users may be able to unprotect the patient data or otherwise recover the protected data.

Patient data protection may be a user-configurable feature of defibrillator 14. In other words, a user may provide an instruction or other input indicating whether the patient data should be protected in response to a download. For example, whether patient data will be protected in defibrillator 14 in response to a download of the patient data may be user selectable option in a menu of configuration option displayed by defibrillator via a user interface. Defibrillator 14 may also allow the user to configure various sub-options related to patient data protection. For example, defibrillator 14 may allow a user to select whether patient data will be protected only in response to receiving an acknowledgment from a downloading device, or which patient data protection techniques will be used to protect data. Defibrillator 14 may also allow a user to set a password for accessing protect patient data or identify a subset of users who will be able to access protected data.

Further, other medical devices may be able to protect patient data in the manner described herein with respect to defibrillator 14. For example, if DMD 24 stores patient data, DMD 24 may protect patient data in the manner described herein in response to downloading the patient data to computing device 28 via network 26. DMD 24 may keep or destroy a local copy of the patient data after the data is sent, depending on the configuration of the DMD. DMD 24 may be configured to protect patient data, e.g., by modifying or deleting the data, in the same manner as defibrillator 14. Therefore, the patient data may be protected in DMD 24 as desired by a user. Further, if computing device 28 stores patient data, the computing device may protect patient data in the manner described herein in response to downloading the patient data to another device.

Figure 3:
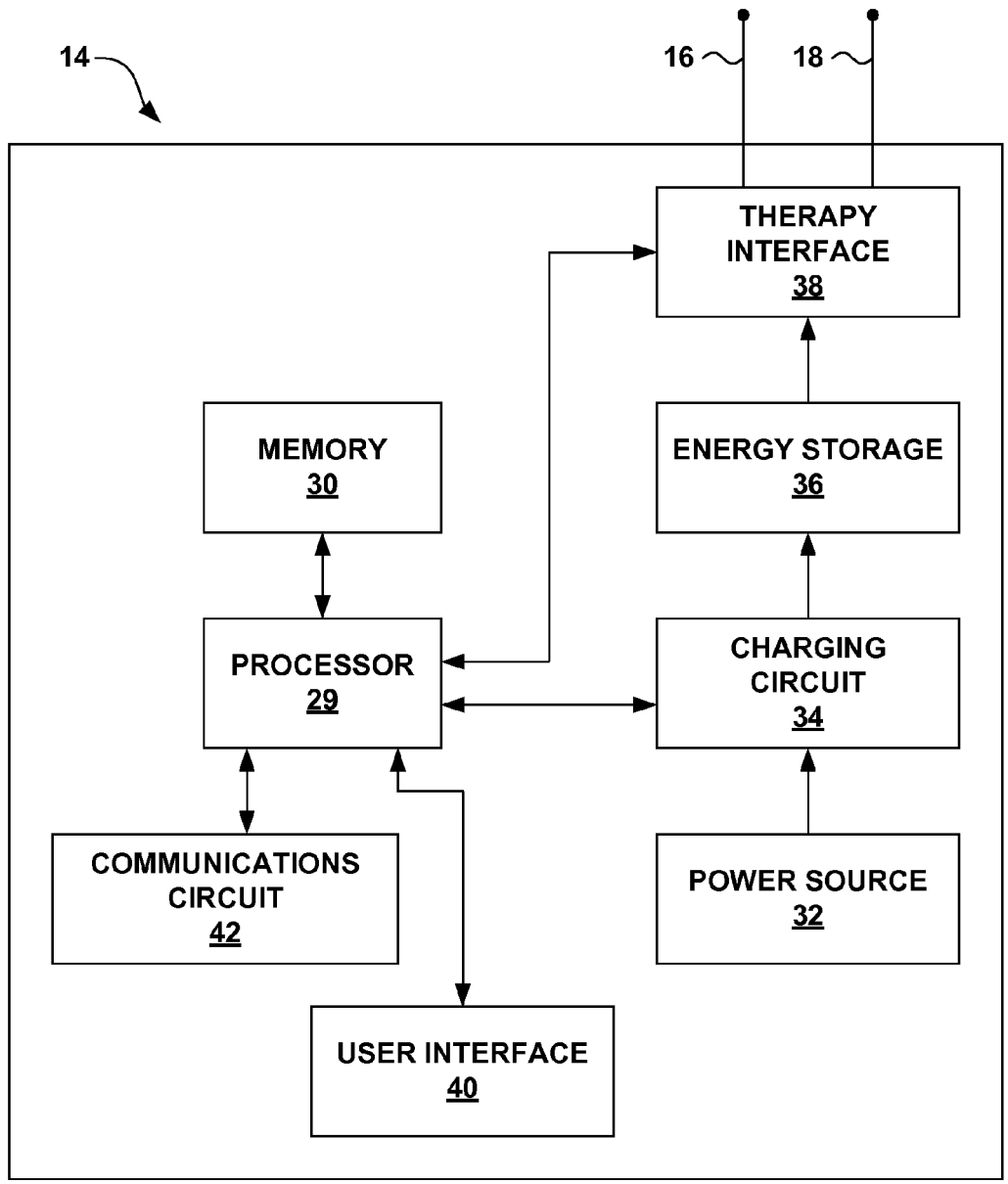
FIG. 3 is a functional block diagram illustrating components of the external defibrillator of FIG. 1.

FIG. 3 is a functional block diagram illustrating components of external defibrillator 14. As shown in FIG. 3, defibrillator 14 may include a processor 29, memory 30, power source 32, charging circuit 34, energy storage 36, therapy interface 38, user interface 40, and communications circuit 42. Leads 16 and 18 are coupled to therapy interface 38.

Processor 29 controls the operations of defibrillator 14 based upon the instructions located in memory 30. Processor 29 controls charging circuit 34 to draw current from power source 32 to charge energy storage circuit 36. Processor 29 controls whether therapy interface 38 detects electrical signals from patient 12, or is coupled to energy storage circuit 36 to deliver the energy stored therein to patient 12 as a defibrillation pulse. Processor 29 also provides prompts and other information to a rescuer, and receives information and commands from a rescuer through user interface 40. Processor 29 sends and receives information to or from other devices though communications circuit 42. Further, as will be discussed in greater detail below, processor 29 stored patient data in memory 30, and protects the patient data in response to downloading the patient data to another device, such as DMD 24 or computing device 28, via communications circuit 40.

Memory 30 stores instructions that cause processor 29 to provide the functionality ascribed to it and defibrillator 14 herein. Memory 30 may include any one or more of a random access memory (RAM), read-only memory (ROM), electronically-erasable programmable ROM (EEPROM), flash memory, or the like. Memory 30 may be fixed within AED 26 or removable from the AED. Processor 29 may comprise any one or more of a microprocessor, digital signal processor (DSP), application specific integrated circuit (ASIC), field-programmable gate array (FPGA), or other digital logic circuitry.

In a typical application, interface 38 includes a receptacle, and conductors 16 and 18 plug into the receptacle. Interface 38 also includes a switch (not shown in FIG. 3) that, when activated, couples an energy storage circuit 36 to conductors 16 and 18. Energy storage circuit 36 stores the energy to be delivered to patient 12 in the form of a defibrillation pulse. The switch may be of conventional design and may be formed, for example, of electrically operated relays. Alternatively, the switch may comprise an arrangement of solid-state devices such as silicon-controlled rectifiers or insulated gate bipolar transistors.

Energy storage circuit 36 includes components, such as one or more capacitors, that store the energy to be delivered to patient 12 via conductors 16 and 18 and electrodes 20 and 22 (FIG. 1). Before a defibrillation pulse may be delivered to patient 12, energy storage circuit 36 must be charged. Processor 29 directs a charging circuit 34 to charge energy storage circuit 36 to a high voltage level. Charging circuit 34 comprises, for example, a flyback charger that transfers energy from power source 32 to energy storage circuit 36.

Defibrillator 14 may be a manual defibrillator or an AED. Where defibrillator 14 is a manual defibrillator, a caregiver using defibrillator 14 may select an energy level for each defibrillation pulse delivered to patient 12. Processor 29 may receive the selection made by the caregiver via a user interface 40, which may include input devices, such as a keypad and various buttons or dials, and output devices, such as various indicator lights, a cathode ray tube (CRT), light emitting diode (LED), or liquid crystal display (LCD) screen, and a speaker. In some embodiments, user interface 40 may include a touch-sensitive display. Where defibrillator 14 is an AED, processor 29 may select an energy level from a preprogrammed progression of energy levels stored in memory 30 based on the number of defibrillation pulses already delivered to patient 28.

When the energy stored in energy storage circuit 36 reaches the desired energy level, processor 29 controls user interface 40 to provide an indication to the caregiver that defibrillator 14 is ready to deliver a defibrillation pulse to patient 12, such as displayed indication or a voice prompt. The defibrillation pulse may be delivered manually or automatically. Where the defibrillation pulse is delivered manually, the caregiver may direct processor 29 to deliver the defibrillation pulse via user interface 40 by, for example pressing a button. In either case, processor 29 activates the switches of interface 34 to electrically connect energy storage circuit 36 to electrodes 20 and 22, and thereby deliver the defibrillation pulse to patient 12.

Processor 29 may modulate the defibrillation pulse delivered to patient 12. Processor 29 may, for example, control the switches of interface 38 to regulate the shape and width of the pulse. Processor 29 may control the switches to modulate the pulse to, for example, provide a multiphasic pulse, such as a biphasic truncated exponential pulse, as is known in the art.

Processor 29 may perform other functions as well, such as monitoring electrical activity of the heart of patient 12 sensed via electrodes 20 and 22. Processor 29 may determine whether the heart of patient 12 is fibrillating based upon the sensed electrical activity in order to determine whether a defibrillation pulse should be delivered to patient 12. Where a defibrillation pulse has already been delivered, processor 29 may evaluate the efficacy of the delivered defibrillation pulse by determining if the heart is still fibrillating in order to determine whether an additional defibrillation pulse is warranted. Processor 29 may automatically deliver defibrillation pulses based on these determinations, or may advise the caregiver of these determinations via user interface 40. Processor 29 may display an electrocardiogram (ECG) that reflects the sensed electrical activity via user interface 40.

Processor 29 may store an indication of the time of delivery of each defibrillation pulse delivered to patient 12 as patient data within memory 30 for patient 12. Processor 29 may also store the energy level of each pulse and other characteristics of each pulse, such as the width, amplitude, or shape, as patient data. Processor 29 may also store a digital representation of the ECG, or a heart rate over time determined based on the electrical activity of the heart of patient 12 detected via electrodes 20 and 22 as patient data. Further, processor 29 may control delivery of other types of therapy to patient 12 via electrodes 20 and 22, such as cardioversion or pacing therapy, and store information describing the times that such therapies were delivered and parameters of such therapies, such as cardioversion pulse energy levels and pacing rates, as patient data for patient 12.

User interface 40 may include a microphone (not shown) that detects sounds in the vicinity of defibrillator 14. Processor 29 may receive signals from the microphone and store an audio recording that includes these signals as patient data. The audio recording may include verbal notations of a user of defibrillator 14, or conversations between the user and patient 12.

The user may mark the time of the occurrence of various events, such as the delivery of drugs or the administration of cardiopulmonary resuscitation (CPR), during the treatment of patient 12 by, for example, pressing a key or button of user interface 40 at the time when the event occurred. Processor 29 may also include these event markers within the patient data stored in memory 30. Where defibrillator 14 is more fully featured, e.g., a manual paramedic or hospital defibrillator, defibrillator 14 may also include additional sensors (not shown) coupled to processor 29, such as sensors to measure blood oxygen saturation, blood pressure, respiration, and the amount of oxygen or carbon dioxide in the air inhaled or exhaled by patient 12. Processor 29 may also store the signals generated by these sensors within memory 30 as patient data for patient 12. In other words, as examples, processor 29 may also store any of a capnograph, a plethysmograph, a blood oxygen saturation over time, a blood pressure over time, a pulse rate over time determined based on measured blood pressure, end tidal carbon dioxide measurements, and/or measurements of the fraction of carbon dioxide in air inspired or expired within memory 30 as patient data. Processor 29 may begin to store patient data when defibrillator 14 is powered on to respond to a medical emergency.

Communications circuit 42 may be used as an interface between defibrillator 14 and another device, such as DMD 24 or computing device 28. Communications may be accomplished through wired or wireless connections. Wired communication connections may include a universal serial bus (USB), a FireWire connection (IEEE 1394), a serial connection, Ethernet connection, modem connection, or any other wired communication technique. Wireless communications may be accomplished by radio frequency (RF) or infrared communication, such as communication according to the Bluetooth, IEEE 802.11 or IRDA protocols.

Power source 32 delivers operating power to the components of AED 26. Power source 32 may include a large battery and a power generation circuit to produce the operating power and therapy. In some embodiments, the battery may be rechargeable to allow extended operation. Recharging may be accomplished by drawing current from a standard alternating current electrical outlet, such as a 120 V outlet. In some embodiments, power source 32 may run directly off of an alternating current outlet.

The patient data stored in memory 30 by processor 29 may include information describing the therapies delivered to patient 12, including the times that the therapies were delivered. The patient data may also include physiological parameter information, including information relating to the times that the physiological parameter information was recorded. The patient data may also include patient personal and identification information, as well as an audio recording.

Processor 29 protects the patient data for patient 12 within memory 30 in response to downloading the patient data to another device via communications circuit 42. Processor 29 protects the patient data such that it is not accessible to at least a subset of users of defibrillator 14. Processor 29 may delete the patient data from memory 30 such that it is no longer available to any users. In other embodiments, processor 29 protects the patient data from being accessed by a first subset of users, but leaves the patient data accessible by a second subset of users. The second subset of users may be a limited number of users, which may be similar to administrative users in the context of a network. The second subset of users may be owners of defibrillator 14, or agents of the manufacturer of defibrillator 14.

In some embodiments, processor 29 modifies, or changes, the data structure of the patient data within memory 30 to a form not readable by DMD 24 or other computing devices that communicate with defibrillator 14. In some embodiments, processor 29 encrypts and/or password protects the patient data such that only the second subset of users, e.g., those who have a password and/or a key to unencrypt the patient data, can access the patient data. Processor 29 may encrypt the patient data with an algorithm stored in memory 30. A password may be entered by a user via user interface 40, or using a computing device via communications circuit, and may be an alphanumeric password or key combination. In other embodiments, a password may be machine-readable, e.g., may be read by defibrillator 14 from a magnetic or radio-frequency identification card.

In some embodiments, user access to at least some of the functionality and resources provided by defibrillator 14 may be controlled by user identification and/or passwords. The user identification or passwords may be alphanumeric, key combination or machine readable. In such embodiments, processor 29 may maintain access control lists (ACLs) in memory 30 for resources of defibrillator 14, including patient data for patient 12 stored in memory 30, associating users or classes of users with a degree of access provided to the user or class for that resource. In such embodiments, processor 29 may protect the patient data for patient 12 by modifying an ACL for the patient data to change the degree of access for a subset of users or classes, and thereby prevent the subset of users from accessing the patient data.

Figure 4:
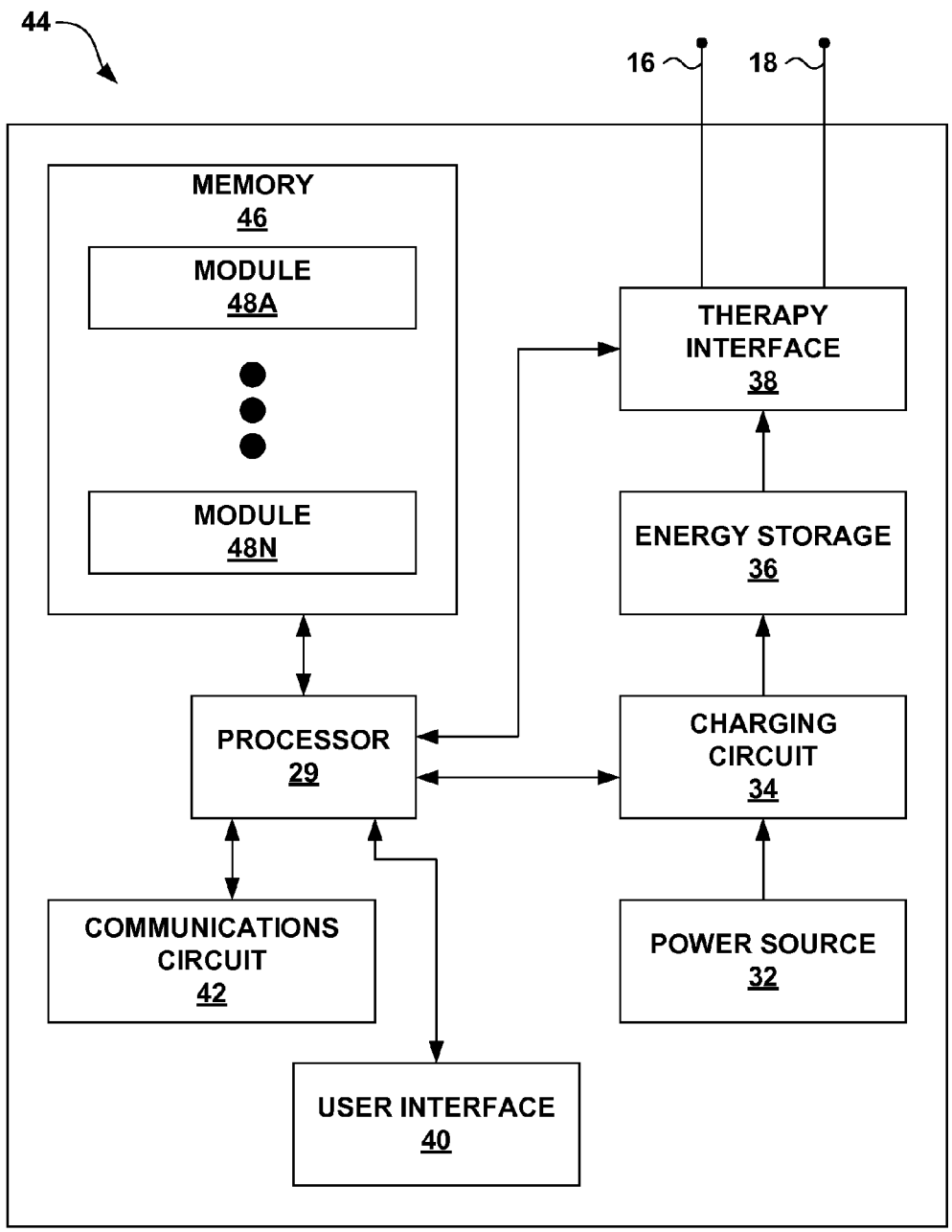
FIG. 4 is functional block diagram illustrating components of another example external defibrillator that collects and stores patient data, the defibrillator including multiple memory modules.

FIG. 4 is functional block diagram illustrating components of another example external defibrillator 44 that collects and stores patient data. Like defibrillator 14, defibrillator 44 may include processor 29, power source 32, charging circuit 34, energy storage circuit 36, therapy interface 38, user interface 40 and communications circuit 42, which are substantially similar to the like-numbered components described above with reference to FIG. 3 and defibrillator 14.

In general, memory 46 is similar to memory 30. However, in the example of FIG. 4, memory 46 is made up of a plurality of modules 48A-48N (collectively, "modules 48"). Modules 48 may, but are not necessarily, physically different circuits for storing data.

In the embodiment illustrated by FIG. 4, processor 29 may store patient data in one of modules 48 during therapy. Once DMD 24 or another device downloads the patient data, processor 29 protects the patient data by moving the patient data to another of modules 48. The other module may be "hidden" or otherwise protected from being accessed by a subset of users via user interface 40 or communications circuit 42. For example, access to the protected module may be protected by a password and/or ACL.

Figure 5:
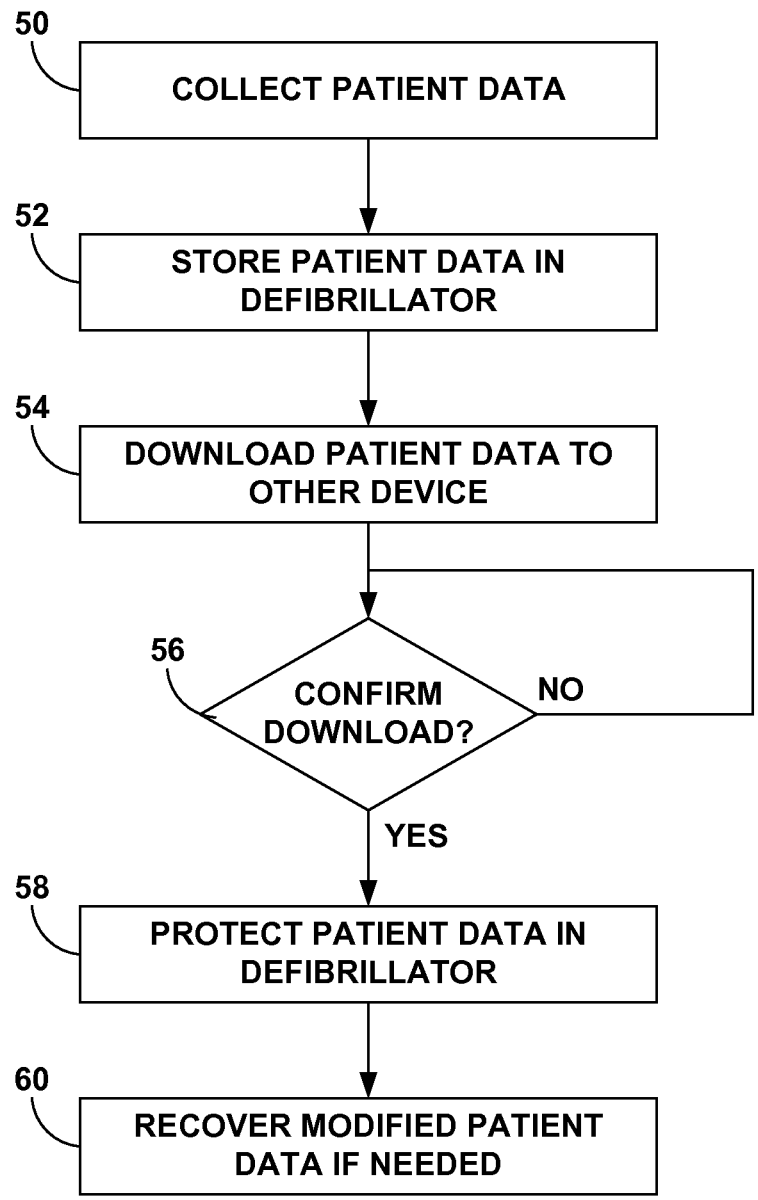
FIG. 5 is a flow diagram illustrating an example technique for protecting patient data stored in an external defibrillator.

FIG. 5 is a flow diagram illustrating an example technique for protecting patient data stored in an external defibrillator. Either of defibrillators 14 and 44 may be used in the example of FIG. 5, but defibrillator 14 will be used as an example. Defibrillator 14, and more particularly processor 29 of defibrillator 14, collects patient data for patient 12 during the treatment of the patient (50). The patient data may include medical and personal information for patient 12, as discussed in greater detail above. Processor 29 stores the patient data in memory 30 for reference during treatment of patient 12 or review (52). Processor 29 downloads the patient data to DMD 24, or to computing device 28 directly via DMD 24 via communications circuit 42 (54). Processor 29 may download the patient data in response to a request from a user received via user interface 40.

In the example illustrated by FIG. 5, processor 29 waits for a confirmation that the download of patient data to DMD 24 was successful (56). The confirmation may be, as examples, a confirmation data packet sent by DMD 24, or a positive cyclical redundancy check (CRC). When processor 29 confirms a successful download, the processor protects the patient data sent to DMD 24 in the memory 30 using any one or more of the techniques discussed in greater detail above (58). In some embodiments, once the patient data is modified, a first subset of users cannot access the patient data, which a second subset of users may access, e.g., recover, the patient data if necessary (60).

The invention is not limited to embodiments in which processor 29 confirms a successful download prior to protecting the patient data. In some embodiments, processor 29 protects the patient data in response to initiation of the transfer of data to DMD 24. In some embodiments, processor 29 protects the patient data in response to completion of the transfer of data to DMD 24 without confirming that the download was successful. In some embodiments, processor 29 protects the patient data some time period, which may or may not be predetermined, after the download begins or ends.

Further, as discussed above, other medical devices may protect patient data in response to downloading the patient data to another device in a substantially similar manner to that described herein with respect to defibrillators 14 and 44. For example, DMDs 24 and computing devices 28 may protect patient data as described herein. Although such devices may not include therapy or monitoring components specific to a defibrillator and illustrated in FIGS. 3 and 4 with respect to defibrillators 14 and 44, the devices may include processors 29, memories 30 or 46, user interfaces 40 and communication circuitry 42 that provide the functionality described above with respect to protection of patient data.

Many embodiments of the invention have been described. Various modifications may be made to the described embodiments without departing from the scope of the claims. These and other embodiments are within the scope of the following claims.

The invention claimed is:

1. A method comprising:
   storing patient data collected by an external defibrillator during treatment of a patient within a medical device;
   allowing users to access the patient data stored in the medical device;
   downloading the patient data from the medical device to another device; and
   in response to downloading the patient data, protecting the patient data in the medical device such that the protected patient data is inaccessible to at least a first subset of authorized users while the protected patient data in the medical device is accessible to a second subset of authorized users, wherein the patient data was accessible to the first subset of authorized users before the patient data was protected.

2. The method of claim 1, wherein protecting the patient data comprises modifying a form of the patient data in the medical device.

3. The method of claim 1, wherein protecting the patient data comprises encrypting the patient data in the medical device.

4. The method of claim 1, wherein protecting the patient data comprises moving the patient data from a first memory location in the medical device to a second memory location in the medical device.

5. The method of claim 1, wherein protecting the patient data comprises requiring a password to access the patient data.

6. The method of claim 1, wherein protecting the patient data comprises modifying an access control list associated with the patient data.

7. The method of claim 1, further comprising determining whether the download of patient data from the medical device to the other device is complete, wherein protecting the patient data comprises protecting the patient data in response to the determination.

8. The method of claim 7, wherein determining whether the download is complete comprises receiving an acknowledgment from the other device at the medical device.

9. The method of claim 1, further comprising determining whether one of the users has configured the medical device to protect patient data in response to downloading the patient data, wherein protecting the patient data comprises protecting the patient data based on the determination.

10. The method of claim 1, wherein the medical device is the external defibrillator.

11. A medical device comprising:
a memory configured to store patient data collected by an external defibrillator during treatment of a patient;
a communications circuit configured to communicate with another device; and
a processor that allows users to access the patient data stored in the memory, controls the communications circuit to download the patient data to the other device and, in response to the download, protects the patient data in the memory such that the patient data is inaccessible to at least a subset of the users, wherein, to protect the patient data, the processor makes the data inaccessible to a first subset of authorized users while leaving the patient data accessible to a second subset of authorized users, wherein the patient data was accessible to the first subset of authorized users before the patient data was protected.

12. The device of claim 11, wherein the processor modifies a form of the patient data in the memory to protect the patient data.

13. The device of claim 11, wherein the processor encrypts the patient data in the memory to protect the patient data.

14. The device of claim 11, wherein the processor moves the patient data from a first location in the memory to a second location in the memory to protect the patient data.

15. The device of claim 11, wherein the processor protects the patient data by requiring a password to access the patient data in the memory.

16. The device of claim 11, wherein the processor modifies an access control list associated with the patient data to protect the patient data in the memory.

17. The device of claim 11, wherein the processor determines whether the download of patient data from the medical device to the other device is complete, and protects the patient data in response to the determination.

18. The device of claim 17, wherein the processor determines whether the download is complete by receiving an acknowledgement from the other device via the communication circuitry.

19. The device of claim 11, further comprising a user interface, wherein the processor receives configuration instructions from one of the users via the user interface, and determines whether to protect the patient data in response to the download based on the configuration instructions.

20. The device of claim 11, wherein the device comprises the external defibrillator.

21. A non-transitory computer readable medium comprising instructions that cause a processor to:
store patient data collected by an external defibrillator during treatment of a patient within a medical device;
allow users to access the patient data stored in the medical device;
download the patient data to another device; and
in response to the download, protect the patient data in the first device such that the protected patient data is inaccessible to at least a first subset of authorized users while the protected patient data is accessible to a second subset of authorized users, wherein the patient data was accessible to the first subset of authorized users before the patient data was protected.

22. The non-transitory computer-readable medium of claim 21, further comprising instructions that cause a processor to determine whether the download of patient data from the medical device to the other device is complete, wherein the instructions that cause a processor to protect the patient data comprise instructions that cause a processor to protect the patient data in response to the determination.

23. The non-transitory computer-readable medium of claim 21, wherein the instructions that cause a processor to store patient data in a medical device comprise instructions that cause a processor to store the patient data in the external defibrillator.

24. A medical device comprising:
a memory configured to store patient data collected by an external defibrillator during treatment of a patient;
a communications circuit configured to communicate with another device; and
a processor that allows users to access the patient data stored in the memory, controls the communications circuit to download the patient data to the other device and, in response to the download, deletes the patient data from the memory.

* * * * *